United States Patent [19]

Schmieding et al.

[11] Patent Number: 5,397,357
[45] Date of Patent: Mar. 14, 1995

[54] METHOD FOR PREPARING A BONE-TENDON-BONE CORE GRAFT

[75] Inventors: Reinhold Schmieding, Naples, Fla.; Craig D. Morgan, Greenville, Del.

[73] Assignee: Arthrex, Inc., Naples, Fla.

[21] Appl. No.: 186,604

[22] Filed: Jan. 26, 1994

Related U.S. Application Data

[63] Continuation-in-part of Ser. No. 19,356, Feb. 18, 1993.

[51] Int. Cl.⁶ .............................................. A61F 2/08
[52] U.S. Cl. ...................................... 623/13; 623/901
[58] Field of Search ....................... 623/11, 13, 901; 606/86; 128/898

[56] References Cited

U.S. PATENT DOCUMENTS

| | | | |
|---|---|---|---|
| 4,927,421 | 5/1990 | Goble | 623/13 |
| 5,211,647 | 5/1993 | Schmieding | 606/104 |
| 5,269,786 | 12/1993 | Morgan | 606/96 |
| 5,320,626 | 6/1993 | Schmieding | 606/96 |

FOREIGN PATENT DOCUMENTS

| | | | |
|---|---|---|---|
| 93/09730 | 5/1993 | WIPO | 623/13 |

OTHER PUBLICATIONS

Brand et al. "Considerations In the Placement Of An Intra-Articular Anterior Cruciate Ligament Graft", *Operative Tech. in Orthop.*, vol. 2, No. 2 (1992) pp. 55–62.

Rubinstein, Jr. et al. "Graft Selection, Placement, Fixation, and Tensioning For Anterior Cruciate Ligament Reconstruction", *Operative Techniques in Sports Medicine*, vol. 1. No. 1 (Jan.) 1993: pp. 10–15.

*Primary Examiner*—Tamara L. Graysay
*Attorney, Agent, or Firm*—Ostrolenk, Faber, Gerb & Soffen

[57] ABSTRACT

A method for preparing a bone-tendon-bone core graft. A bone core is harvested from a patient and divided into two separate bone core halves. The bone core halves are inserted onto holding pins which are movably spaced along a work station. A harvested tendon is secured with suture onto the bone core halves, with the tendon extending therebetween to form the bone-tendon-bone core graft. The holding pins are supported by blocks which are moved apart along the work station to tension the bone-tendon-bone graft.

9 Claims, 6 Drawing Sheets

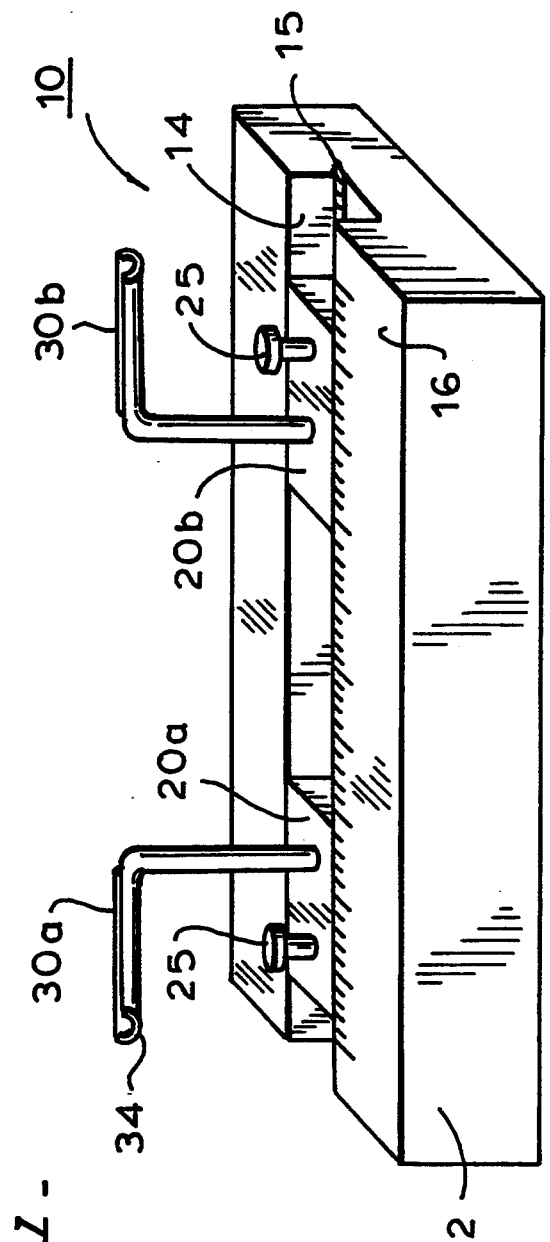
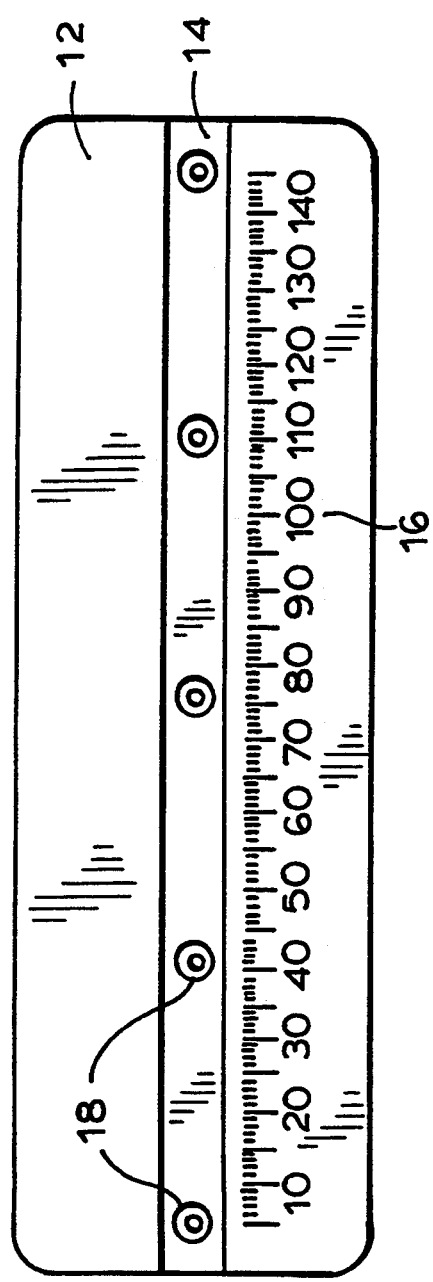

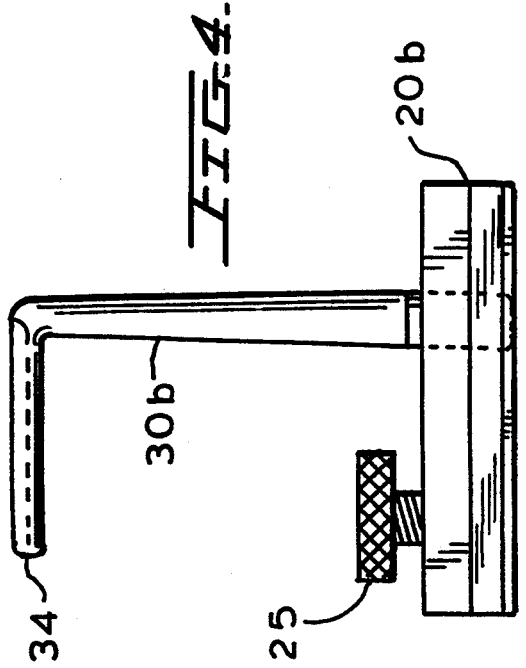
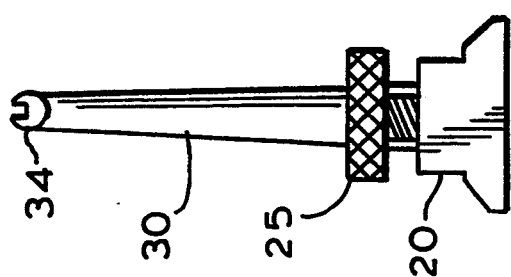
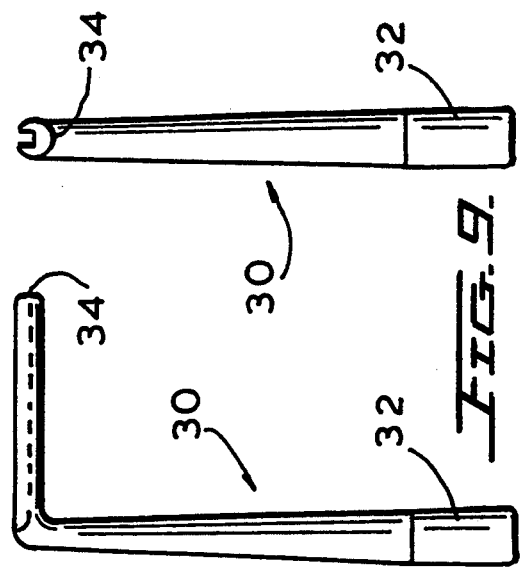
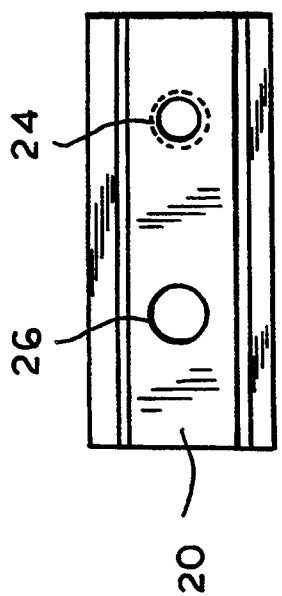

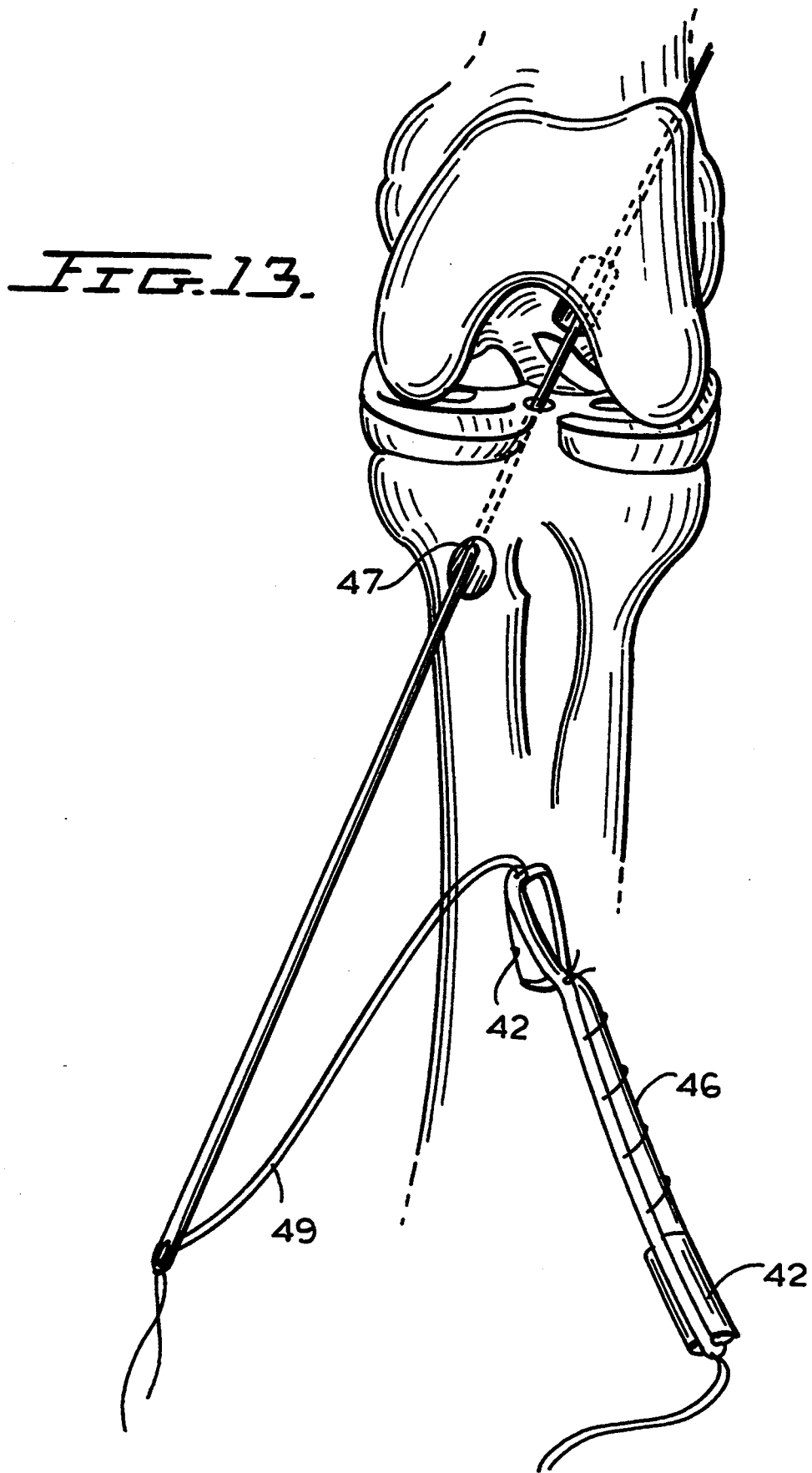

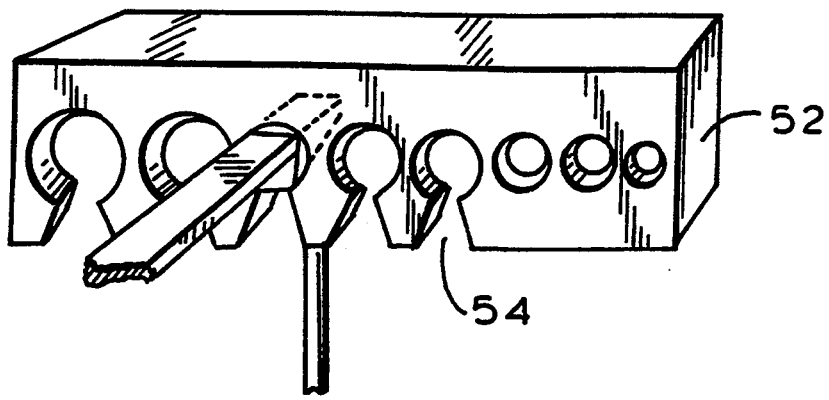
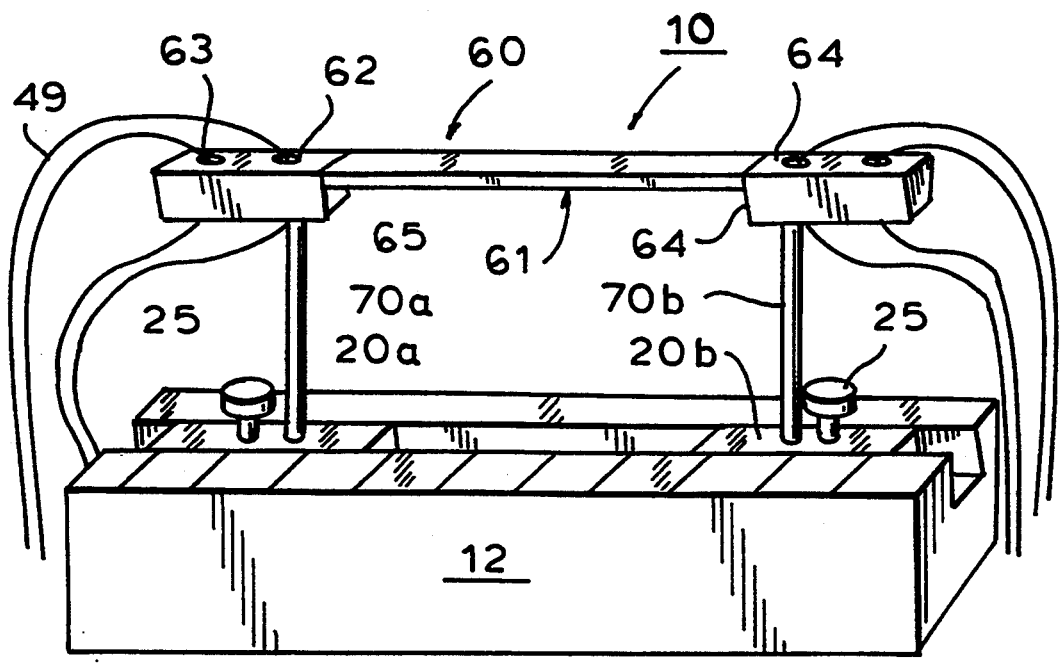
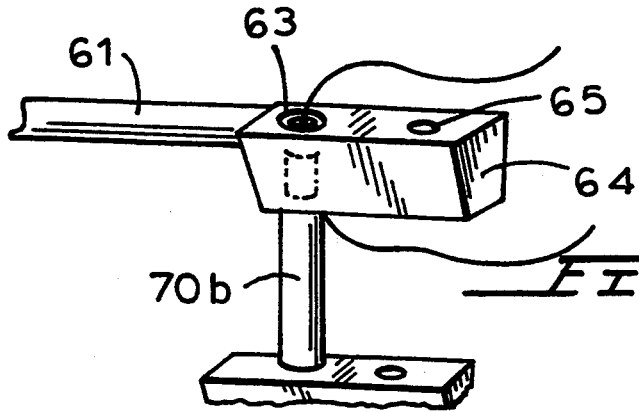

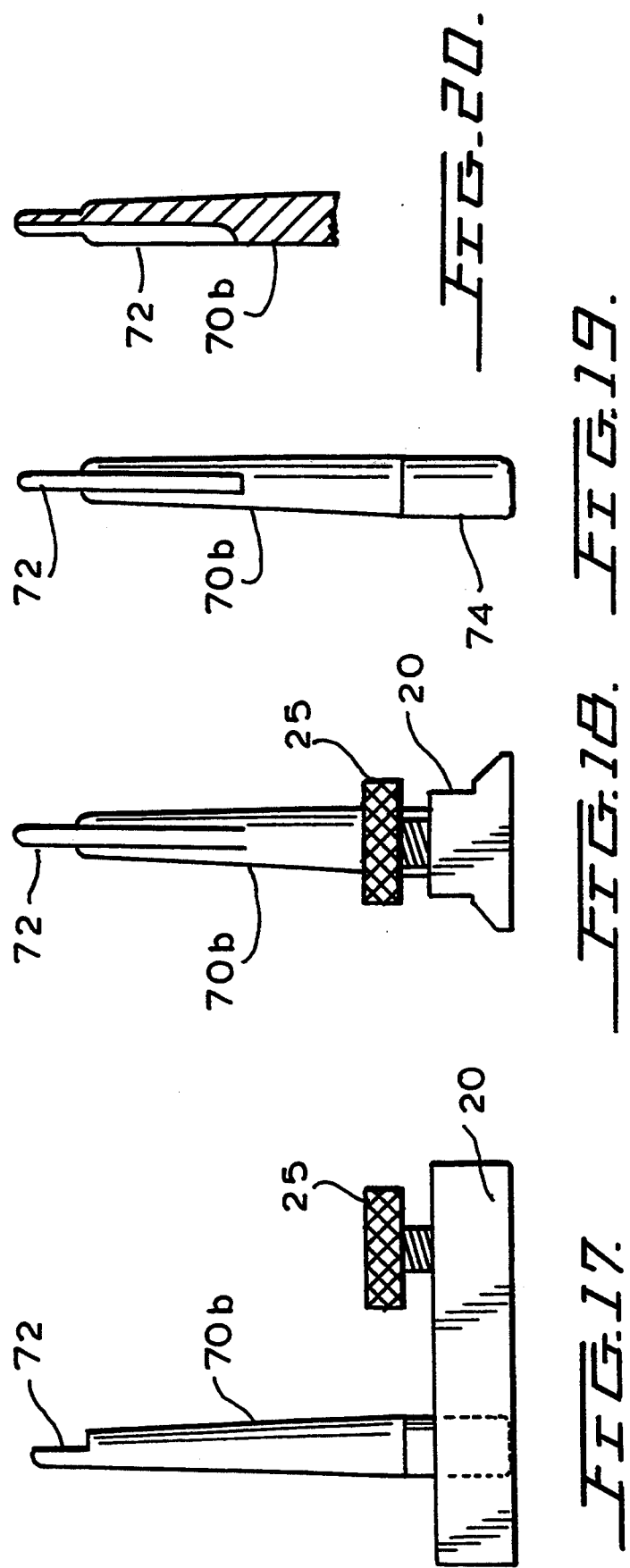

METHOD FOR PREPARING A BONE-TENDON-BONE CORE GRAFT

This is a continuation-in-part of U.S. application Ser. No. 08/019,356, filed Feb. 18, 1993, the disclosure of which is herein incorporated by reference.

BACKGROUND OF THE INVENTION

1. Field of the Invention

The present invention relates to a method for preparing a bone-tendon-bone graft for anterior cruciate ligament reconstruction.

2. Description of the Related Art

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones, for example, the tibia and the femur.

To achieve optimal results, it is important that the graft tunnel be drilled at a particular angle and location through the tibia and femur. This can be accomplished by using a variety of tools, such as sighting devices or marking hooks. See U.S. Pat. Nos. 5,269,786 and 5,320,620, assigned to the same assignee as the present application, for examples of such devices.

A surgical device for coring the bones can be used to create the graft tunnel and includes means for conveniently removing the cut-out bone from the instrument. The coring reamer of parent application Ser. No. 08/019,356 creates a tibial or femoral tunnel and simultaneously produces a cancellus bone graft which can be used, for example, to fill a patella tendon graft harvesting site at the tibial tubercle and patella of the knee during ACL reconstruction.

The coring reamer of application Ser. No. 08/019,356 includes an elongated collared guide pin which is inserted through the guide pin tunnel in the tibia. A cannulated core saw is inserted over the collared guide pin for drilling the tibia tunnel. A collar is spaced a predetermined distance from one end of the guide pin. As the core saw advances over the collared guide pin in drilling the tunnel, the bone mass generated by the drilling procedure fills the core of the reamer and pushes the collar back into the core.

Upon completion of drilling, the pin, saw, and the contained bone mass are removed from the patient's body. The core of bone mass is then removed from the core saw by tapping the end of the collared guide furthest from the collar. The core of bone mass can then be cut in half and used as bone blocks for subsequent hamstring graft fixation or filling of a harvested graft site.

The bone blocks can be wedged to the wall of a graft tunnel formed through the bone using an interference screw. See U.S. Pat. No. 5,211,647, assigned to the same assignee of the present application, for an example of this device.

A patellar tendon having attached tibial tubercle and patellar bone plugs is often used as an ACL graft. The bone-patellar tendon-bone graft is harvested together in one piece removing one bone block from the patella and one bone block from the tibia, with the tendon extending therebetween. However, since separate bone blocks must be harvested, several incisions must be made in the patient's knee to remove the patellar tendon-bone graft.

Special attention is required when tensioning both the patellar-tendon graft and the bone-hamstring tendon-bone graft. In particular, proper tensioning of the graft prior to fixation decreases elongation of the graft once it is in place. The tension of the graft must be sufficient in order to achieve stability, but not so excessive that it captures the joint. See, e.g., Rubenstein et al., "Graft Selection, Placement, Fixation, and Tensioning for Anterior Cruciate Ligament Reconstruction", *Operative Tech in Sports Med.*, Vol 1, No. 1, p. 13 (1993).

Ordinarily, the graft is inserted through the prepared tunnel and tensioned prior to being secured by moving the knee through a range of motion. One method of determining the proper tension is by using an isometer to measure the tension change at different points. See e.g., Brand et al., "Considerations in the Placement of an Intra-articular Anterior Cruciate Ligament Graft", *Operative Tech. in Orthop.*, Vol. 2, No. 2 (1992). However, tensioning of the graft after the graft is partially in place in the tibial tunnel is cumbersome.

SUMMARY OF THE INVENTION

The present invention overcomes the above-noted deficiencies by providing a method for the tensioning of patellar tendon bone grafts and for the preparation and tensioning of a bone-hamstring tendon-bone graft.

In the method of the present invention, a bone core harvested from a patient is divided into two halves. The bone core halves are inserted onto horizontal holding pins, which are supported by blocks movably disposed along the work station. A tendon is harvested and secured on the bone core halves, with the tendon extending between the bone core halves to form the bone-tendon-bone graft. The holding pins are moved apart along the work station to tension the bone-tendon-bone graft.

In the preparation of a bone-hamstring tendon-bone core graft, an axial hole is drilled partially through and along the central axis of each of the bone core halves. The axial holes of the bone core halves are respectively inserted over the horizontally disposed holding pins of the work station.

The tendon is secured to a first of the two bone core halves by passing suture through the axial hole of the first bone core half and through the tendon and bone core, and tying the tendon thereto. The tendon is then wrapped around the second bone core half and fixed thereto to form a double strand graft. A third strand of suture is wrapped around, parallel with the first and second strands, to form a triple strand graft.

Next, the holding pins are positioned on the base corresponding to the proper graft length and are moved apart to tension the graft, and a whip stitch is tied along the length of the tendon between the bone core halves to secure the three strands of tendon together along their length.

The work station for preparing a bone-tendon-bone graft comprises a base having a longitudinally extending groove. First and second blocks are movably disposed in the groove of the base. Means are provided for securing the blocks in the groove. The blocks each support a holding pin which receives a respective bone core. A tendon is secured on and between each of the bone cores, such that when the blocks are moved apart from each other along the groove, the tendon is tensioned between the bone cores.

The bone-tendon-bone graft allows bone-to-bone fixation when the graft is inserted within a prepared tunnel. Added advantages, such as not disturbing the extensor mechanism, thereby reducing post-operative extensor pain, arthrofibrosis and range of motion loss are achieved by using a bone-tendon-bone graft as the allograft. Moreover, no large midline incision is necessary.

Other features and advantages of the present invention will become apparent from the following description of the invention, when read in conjunction with accompanying drawings.

BRIEF DESCRIPTION OF THE DRAWINGS

FIG. 1 is a perspective view of the work station of the present invention.

FIG. 2 is top view of the base of the work station.

FIGS. 3 and 4 are side views of the holding pins and block assemblies.

FIG. 5 is a front view of the assemblies of FIGS. 3 and 4.

FIG. 6 is a top view of and FIG. 7 is a side view of the block of the present invention.

FIG. 8 is a side view and FIG. 9 is a front view of the holding pin of the present invention.

FIG. 13 is a perspective view of the bone-tendon-bone graft being inserted into the tibial tunnel.

FIG. 14 is a perspective view of a graft size tester.

FIG. 15 is a perspective view of the work station modified to accommodate a patellar tendon autograft.

FIG. 16 is an enlarged view of the bone block and vertical holding pin used with the work station.

FIG. 17 is a side view of the vertical holding pin block assembly.

FIG. 18 is a front view of the assembly of FIG. 17.

FIG. 19 is a front view of the vertical holding pin.

FIG. 20 is a partial cross-section of the vertical holding pin.

DETAILED DESCRIPTION OF THE PREFERRED EMBODIMENTS

Figure 10:
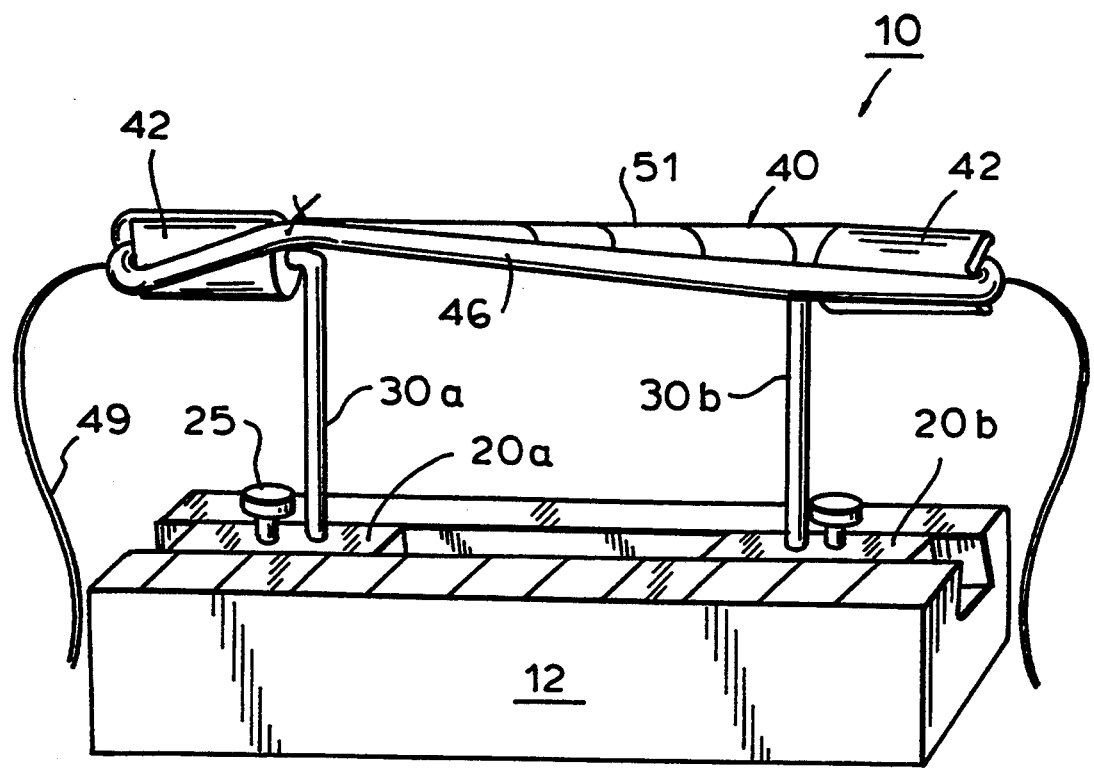
FIG. 10 is a perspective view of the work station with the bone-tendon-bone core graft in place.

As described in co-pending parent application Ser. No. 08/019,356, a coring reamer is used for creating a tibial and femoral tunnel and for simultaneously producing a bone graft for arthroscopic anterior cruciate ligament reconstruction. The harvested bone mass having, for example, a 9 mm diameter and a length of between 50–55 mm, is cut into two equal halves of 20 mm each, using an oscillating saw or osteotome. The sectioned bone mass is used to produce a bone-hamstring tendon-bone graft, as described herein.

FIG. 1 illustrates the tendon graft work station 10 of the present invention. The work station includes a base 12 having a groove 14 extending along its length. The groove 14 is shaped to accommodate support blocks 20a, 20b, which are each movably disposed in groove 14.

As shown in FIG. 2, a plurality of holes 18 are located within the groove 14 at spaced intervals. A screw 25 is inserted through an opening 24 in each of the support blocks (see FIG. 6) and into one of the holes 18 to secure the blocks in place on the base—see FIG. 3 and FIG. 4. Base 12 includes millimeter indicia 16 for measuring the length and/or load on the graft during tensioning.

Each of the support blocks 20a, 20b has a flared bottom edge 22, see FIG. 7, which is adapted to be engaged in a corresponding recess 15 in groove 14, to prevent the blocks from sliding up out of the groove as the graft is tensioned.

L-shaped horizontal holding pins 30a, 30b are mounted on support blocks 20a, 20b, respectively. Each support block 20a, 20b includes an aperture 26 for receiving an end 32 of one of the holding pins 30a, 30b. Each holding pin 30 extends upwardly from the base 12 and includes a horizontal portion 34 for holding a respective bone block. As illustrated in FIGS. 8 and 9, horizontal portion 34 is U-shaped—this shape accommodates the passage of a needle and suture during the securing of the tendon on the bone block.

FIG. 10 illustrates a bone-hamstring tendon-bone graft 40 in place on the work station 10. Bone cores 42 are inserted over pins 30a, 30b, with the U-shaped portion of the pins extending through the lumina of the bone cores. The support blocks 20a, 20b are spaced apart a distance corresponding to the desired graft length.

Figure 11:
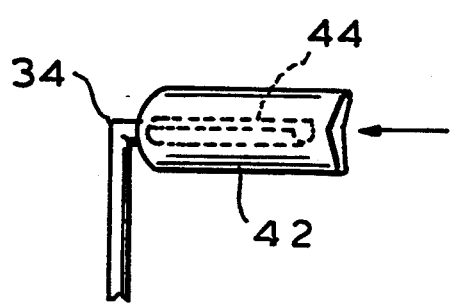
FIGS. 11 and 12 are enlarged views of a bone core in place on a holding pin.
Figure 12:
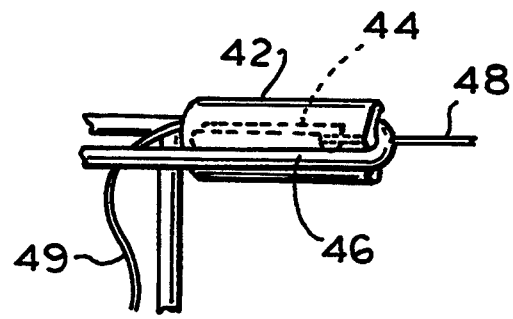

FIG. 11 is an enlarged view of a bone core 42 positioned over the horizontal U-shaped portion 34 of pin 30b. FIG. 12 illustrates the tendon 46 being wrapped around the bone core 42. As discussed previously, the horizontal portion 34 of pins 30 is U-shaped, allowing the passage of a needle 48 and suture 49, through the bone core and the tendon, to enable the tendon to be sutured to the bone core.

The operation of preparing a single incision bone-hamstring tendon-bone autograft will be discussed with reference to FIGS. 10–12. During preparation of the bone-hamstring-tendon-bone graft, for example, a 30 cm length of semitendinosus tendon is harvested with a tendon stripper through an incision made over the pes anserinus. This incision can also be used for the tibial and femoral tunnel placement. The procedure provides a round triple strand graft which is 10–12 mm in diameter and approximately twice the cross-section of a bone-patellar tendon-bone autograft. During surgery a 2½ to 3 cm insertion is made exposing the pes anserinus—this same insertion is used to create the tibial tunnel. The semitendinosus tendon is identified and released from its tibial insertion near the tibial tubercle for maximum tendon length.

Traction sutures are placed in the distal end of the tendon and, with the knee flexed at 90°, the tendon stripper is used to harvest the semitendinosus tendon. An average semitendinosus tendon has a length of 30 to 40 cm and will yield a triple strand bone-hamstring-bone graft between 80–90 mm in length.

After harvesting, residual muscle fibers are stripped from the proximal end of the tendon. The proximal end of the tendon is tubified with sutures to form the entire tendon into a round bundle. Next, the entire tendon length is measured and divided by three to determine the optimal graft length of the harvested tendon.

A tensioning suture is placed at the free end of the tendon. After the graft tunnel has been formed with the coring reamer, the bone blocks are prepared as discussed above. To measure the exact graft length necessary for a particular patient, a guide pin is passed into the femoral tunnel and marked at the entrance to the tibial tunnel. This segment is measured after the guide pin has been removed.

The pins are positioned at the appropriate graft length on the work station base. The tendon is positioned around the bone cores and sutures are passed around the periphery of the tendon and bone blocks to temporarily hold the tendon in place.

As shown in FIG. 12, the midsubstance of the hamstring tendon 46 is perforated with suture needle 48 and the needle is inserted into the center hole or lumina 44 of the bone core held by the U-shaped horizontal holding pin 30. Nonabsorbable suture is then passed through the tendon and bone core and the tendon is tied to the bone core end. The ends of the sutures are left of a sufficient length to assist in graft placement.

The tendon is then wrapped around the second bone core and fixated in a similar manner in accordance with the desired overall graft length to form a double strand graft. The remaining length of the tendon is positioned parallel to the first two strands. The free ends of the sutures which were passed through the bones cores are used to secure the third strand to each back of the bone cores. Thus, a solid permanent suturing of the triple strand tendon is provided on both of the bone cores, such that no separation between the tendon and bone cores will occur during graft insertion.

The holding pins and blocks are then drawn apart on the work station to tension the graft. As shown in FIG. 10, a running suture 51 (in the form of a whip stitch or a figure 8 pattern) is used to secure the three strands of the tendon together to form a cohesive bundle which facilitates passage of the graft through the bone tunnels during insertion in the knee. Additional sutures may be tied around the end of the graft to compress the same for ease of insertion. Graft tensioning and passing sutures are placed through each end.

The diameter of the completed graft is measured while it is still attached to the work station. If necessary, it is possible to overream the femoral and tibial tunnels so that the graft can be inserted therethrough easily.

When properly constructed, the composite triple thickness semitendinous bone core autograft should have one-fourth of the bone plug longitudinal surface with exposed bone for interference screw fixation, as discussed in U.S. Pat. No. 5,211,647. Sufficient lengths of the sutures are maintained on either side of the graft for aid in placement within the tibial tunnel.

As shown in FIG. 13, the combined bone-hamstring-tendon-bone graft is inserted into the tibial and femoral tunnel 47 using a transtibial technique. A needle threaded with the suture ends 49 is used to pull the graft into place. Sheathed interference screws can then be used to fixate the bone cores securely in the bone tunnels.

FIG. 14 illustrates a graft sizing block 52 having various different sized openings 54, which allows graft size assessment while the graft is in place on the work station by inserting the openings of block 52 over the graft ends. Additional grooving and shaping may be performed along the sides of the bone core when graft diameter reduction is required.

FIGS. 15–20 illustrate another embodiment of the holding pins for accommodating the fixation of a patellar tendon autograft 60 for modeling, suture placement, diameter testing and pre-tensioning of the graft.

As shown in FIG. 15, vertical pins 70a, 70b are used in the blocks 20a, 20b to accommodate a patellar tendon autograft 60. As discussed previously, the patellar-tendon autograft is harvested from a patient in one piece by removing a first bone core 62 from the tibia of a patient, stripping the attached tendon 61 and then removing a second bone core 64 from the patella, attached to the other end of the tendon. Thus, with the patellar-tendon autograft, no suturing of the harvested tendon is required to attach the tendon to the bone cores. For mounting and tensioning purposes, however, the work station and pin block assemblies operate in the same manner as discussed above.

When the bone cores 62, 64 are harvested from the patient, holes 63, 65 are drilled therethrough. These same holes 63, 65 are used in this embodiment of the present invention to mount the bone cores 62, 64 over the vertical holding pins 70a, 70b. FIG. 16 is an enlarged view of bone core 64 mounted on pin 70b.

FIG. 17 illustrates the pin block assembly including vertical pin 70b, which is easily exchangeable with the U-shaped horizontal holding pins. Similarly, FIG. 18 is a front view of the pin and block assembly.

FIGS. 19 and 20 illustrate the vertical holding pins. Each pin includes an end 74 which is insertable into aperture 26 in the support blocks 20. As shown in FIG. 20, the upper end 72 of each of the vertical pins is U-shaped to accommodate the passage of suture material 49 through the bone cores.

The patellar-tendon bone core graft is secured with sutures to assist in graft placement and tensioned on the work station.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for preparing a bone-tendon-bone graft using a tendon graft work station having first and second holding pins movable with respect to each other along the work station, comprising the steps of:
   mounting first and second bone core halves onto the first and second holding pins, respectively;
   securing a harvested tendon on the first and second bone core halves, the tendon extending between the bone core halves to form the bone-tendon-bone graft; and
   tensioning the bone-tendon-bone graft by moving the holding pins apart along the work station.

2. The method of claim 1, further comprising the step of drilling an axial hole partially through and along the central axis of each of the bone core halves before the mounting step.

3. The method of claim 2, wherein each of the holding pins include a horizontal portion and the step of mounting comprises sliding the axial hole of each of the bone core halves over the horizontal portion of the respective holding pin.

4. The method of claim 3, wherein the step of securing the harvested tendon on the first bone core half comprises suturing a first end of the tendon to the first bone core half by passing a suture through the axial hole of the first bone core half and through the tendon.

5. The method of claim 4, wherein the step of securing the harvested tendon on the first and second bone core halves further comprises, after suturing the first end of the tendon to the first bone core half, wrapping a free end of the tendon around the second bone core half and suturing the tendon to the second bone core half, thereby forming a double strand of tendon between the first and second bone halves.

6. The method of claim 5, wherein the step of securing the harvested tendon on the first and second bone core halves further comprises, after suturing the tendon to the second bone half, wrapping the free end of the tendon back to the first bone half and suturing the free end of the tendon to the first bone half, thereby forming a triple strand of tendon between the first and second bone halves.

7. The method of claim 6, further comprising, after tensioning of the bone-tendon-bone graft, the step of whip stitching together the triple strands of tendon extending between the bone core halves.

8. The method of claim 1, further comprising, before the step of mounting the first and second bone core halves onto the first and second holding pins, the steps of harvesting a bone core from a patient and dividing the harvested bone core into the first and second bone core halves.

9. A method for tensioning a patellar tendon autograft using a tendon graft work station having first and second holding pins movable with respect to each other along the work station, comprising the steps of:
 mounting first and second bone cores of a bone-patellar-bone autograft onto the first and second holding pins, respectively; and
 tensioning the bone-patellar-bone autograft by moving the holding pins apart along the work station.

* * * * *